Figure 1:
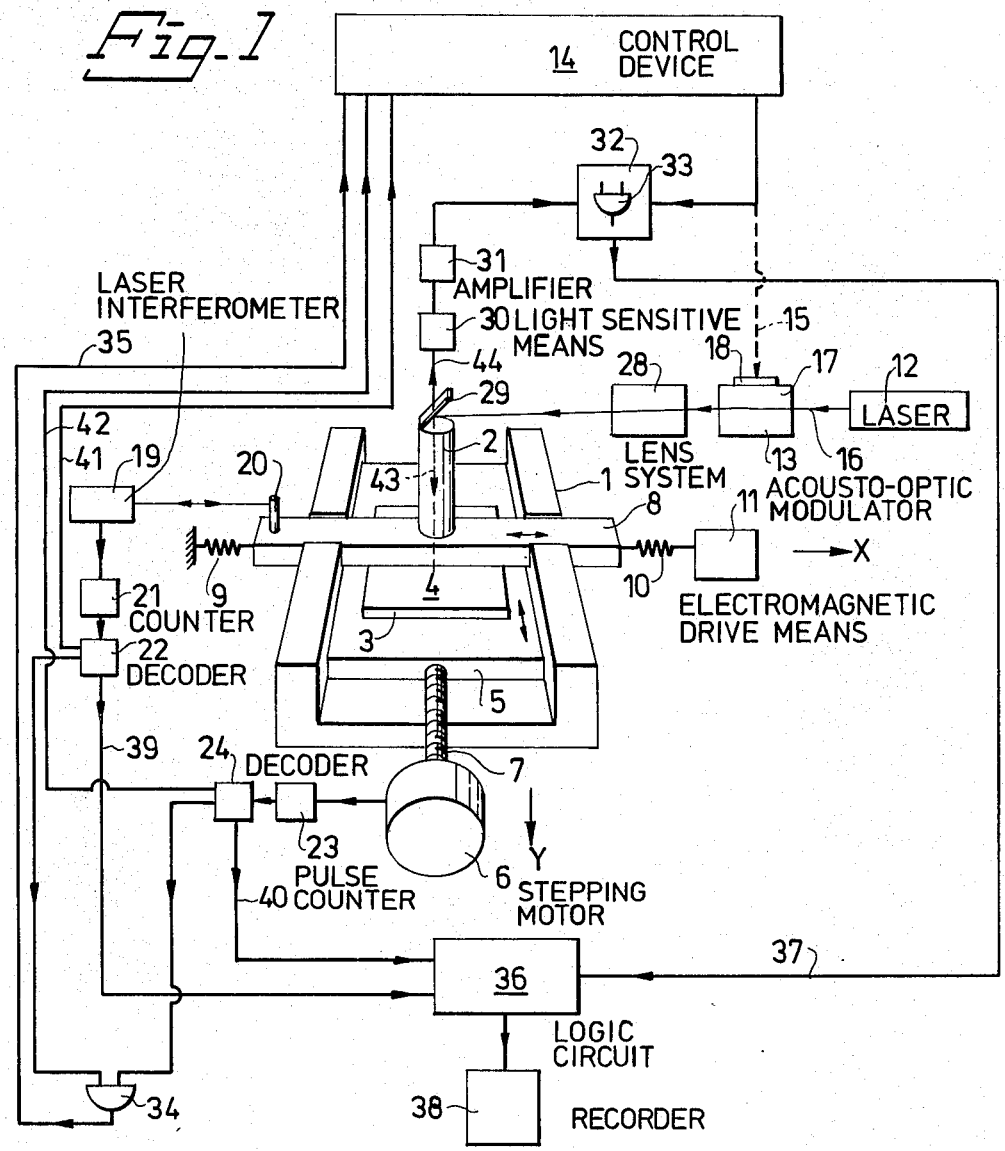

United States Patent [19]

Westerberg

[11] Patent Number: 4,465,350

[45] Date of Patent: Aug. 14, 1984

[54] METHOD AND DEVICE FOR INSPECTING MICROMASK PATTERNS

[76] Inventor: Gerhard Westerberg, Danderydsvägen 36, 182 65 Djursholm, Sweden

[21] Appl. No.: 328,681

[22] Filed: Dec. 8, 1981

[30] Foreign Application Priority Data

Dec. 11, 1980 [SE] Sweden .............................. 8008725

[51] Int. Cl.³ .............................................. B41B 41/00
[52] U.S. Cl. ......................................... 354/4; 364/491
[58] Field of Search ........................... 354/4; 346/108; 364/491

[56] References Cited

U.S. PATENT DOCUMENTS

| | | | |
|---|---|---|---|
| 3,670,153 | 6/1972 | Rempert et al. | 364/491 |
| 3,844,461 | 10/1974 | Robison et al. | 354/4 |
| 3,881,098 | 4/1975 | Rich | 354/4 |
| 3,903,527 | 9/1975 | Frehling | 354/4 |
| 3,985,439 | 10/1976 | Kiemle | 354/4 |
| 4,060,816 | 11/1977 | Westerberg | 354/4 |
| 4,231,659 | 11/1980 | Logan | 354/4 |
| 4,295,198 | 10/1981 | Copeland et al. | 364/491 |
| 4,305,097 | 12/1981 | Doemens et al. | 364/491 |

*Primary Examiner*—Russell E. Adams
*Attorney, Agent, or Firm*—Silverman, Cass & Singer, Ltd.

[57] ABSTRACT

Inspection of micromask patterns occurs by both moving an inspecting laser beam relative to a micromask and varying the intensity of said beam in the same manner that occurs during pattern generation. The pattern modulates the inspecting laser beam by one of reflecting or transmitting a modulated laser beam therefrom. The modulated beam then is sensed and used to produce a modulation signal. The modulated signal is compared to a control signal, which controls both the relative movement between a writing laser beam and the micromask and varies the beam intensity during pattern generation. Agreement between the modulation and control signals indicates correct pattern generation and a difference therebetween indicates a pattern inaccuracy.

6 Claims, 2 Drawing Figures

METHOD AND DEVICE FOR INSPECTING MICROMASK PATTERNS

This invention relates to a method and a device for the inspection of generated micromask patterns.

Such micromasks are utilized in the manufacture of integrated circuits.

In SE-PS Nos. 375 216 and 7501605-5 and in U.S. Pat. Nos. 3,903,536 and 4,060,816 methods and means for generating micromasks are described.

The devices described there comprise means for effecting a relative movement between a radiation source and a radiation-sensitive medium. Said means comprise a first slide capable of performing a relatively slow movement in one direction, and a second slide capable of performing a rapid reciprocatory movement in a direction perpendicular to said firstmentioned direction. These two motions are used to scan a surface of the radiation-sensitive medium by means of a beam from the radiation source, thereby exposing the radiation-sensitive medium.

The technique described is highly applicable and accurate. For example, the pattern of the generated mask has a tolerance of ±0.25 μm.

With this technique a mask having an extremely complicated pattern can be generated which normally has a surface greater than 10×10 cm.

This mask technique, however, involves one great problem, viz. the quality control that a generated mask is correct. At present, generated masks are quality controlled or inspected manually by studying the mask in a microscope. Such study of only one mask having a pattern of normal complexity requires about one working day and is very strenuous. There is, moreover, the risk that inaccuracies are not detected at the inspection.

The present invention eliminates entirely the aforesaid shortcomings, as its object is to provide a method and a device for automatic inspection of a generated micromask.

The present invention, thus, relates to a method of quality controlling micromasks, the pattern of which exists in the form of information stored in a memory. The stored information indicates the position of the micromask when it is generated relative to a laser beam incident perpendicularly thereto and varying in intensity and/or position at any point thus generated of the micromask, and information with respect to the variation of the laser beam in intensity and/or position. The invention is characterized by a micromask to be quality controlled being caused, by means providing relative movement in two perpendicular directions between the optics of a laser and the micromask, to move relative to a laser inspection beam incident from said laser and perpendicular to the micromask in the same way as during generation of the micromask. The inspection laser beam is caused to be reflected against or be transmitted through the micromask, and the laser light thus reflected or transmitted is scanned by a light-sensitive means having an output signal that is applied to a comparison circuit at the same time as and synchronously with the application of a control signal to the comparison circuit. The control signal corresponds to a control signal emitted during the generation of the micromask with respect to said variations in intensity and/or position of the laser beam, which control signal is stored in said memory. Agreement between the signals thus compared indicates a correct generation of the micromask, and disagreement between the signals indicates an inaccuracy.

The invention further relates to a device for controlling micromasks according to said method.

The invention is described with reference to the accompanying drawing, in which

Figure 2:

FIG. 1 shows schematically a device with the invention subject matter applied thereto, by way of a combination of a block diagram and outline, and FIG. 2 is a basic cross-section of a pattern plate.

In FIG. 1, a mechanical device 1 moves a part of the optics 2 of a radiation source in two perpendicular directions relative to a pattern plate 3, which comprises a substrate 4 for generating a micromask.

In the embodiment of the device shown by way of example, which device corresponds to that shown in SE-PS No. 7501605-5, a first slide 5 is provided for performing a relatively slow movement in the y-direction by means of a stepping motor 6 with associated screw 7. A second slide 8 is capable of performing a relatively rapid reciprocatory movement in the x-direction by means of the springs 9,10 and an electromagnetic drive means 11. The second slide 8 is an oscillating mass in a mechanical system.

The part 2 of the optics is located on the second slide.

During the generation of a micromask 4, the second slide 8 is rapidly reciprocated while the first slide 5 moves slowly. This implies that the light from a laser 12 passed through the optics 2 scans in a line pattern over the radiation-sensitive substrate 4. By varying the light intensity meeting the substrate 4, a pattern, i.e. a micromask, is obtained.

According to U.S. Pat. No. 3,903,536, an acousto-optic modulator 13 is provided, to which a modulated high-frequency signal from a control device 14 is applied via a conductor 15 indicated by dashed line in FIG. 1. The modulator 13 diffracts the beam 16 from the laser 12 and modulates the intensity of the beam at its passage through the modulator 13. The acousto-optic modulator 13 comprises a glass body 17, which is abutted by one or several piezo-electric crystals 18. To this crystal or these crystals said signal is applied, whereby ultrasonic waves are formed in the glass body 17. As a result of the ultrasonic waves, a screen of different densities is formed in the glass body and gives rise to diffraction of the beam 16.

The variation of the laser beam 16 in combination with the relative movement of the optics 2 of the radiation source towards the radiation-sensitive substrate, thus, yields a micromask in accordance with the signal applied to the modulator 13 from the control unit.

In order to continuously determine the position of the substrate 4 relative to the optics 2, a position transducer is provided, which consists of a transducer on the stepping motor 6, which may be a pulse counter 23, and a laser interferometer 19,20 of a kind known, for example, according to U.S. Pat. No. 3,903,536. A counter 21 and a decoder 22 of known type are connected to said laser interferometer 19,20 for generating a signal corresponding to the position of the second slide 8 relative to the substrate. A corresponding decoder 24 is connected to the pulse generator for generating a signal corresponding to the position of the first slide 5 relative to the substrate.

During the generation of a micromask, thus, the signal emitted to the modulator 13 is synchronized via the control device 14 with the position of the optics 2 relative to the substrate 4.

The control device 14 is of known kind according to the aforesaid patent and comprises registers for receiving information from a memory, including the configuration of the desired micromask, and means for generating said signal to the modulator 13 according to said information.

In the foregoing, an embodiment of a device for effecting relative movement between a part of the optics 2 and a substrate 4 and for generating a micromask has been described.

It is obvious that other mechanical or electronic/mechanical devices can be used for effecting said relative movement.

The present invention is described below on the basis of the device referred to above by way of example and can be applied to masks generated by any optional device where the information is emitted from a control device in the form of a control signal, including modulation of the beam 16 emitted in response to position indications concerning the point of impact of the beam on the substrate relative to the surface of the substrate.

The pattern plate 3 comprises a glass plate 25, on which a layer 26 of, for example, chromium or chromium oxide is attached, which layer is covered with a layer 27 of so-called photo-resist. By means of the laser 12, which may be an He—Cd laser, the layer 27 of photo-resist is exposed, which at development disappears in exposed or non-exposed portions. The layer of chromium or chromium oxide thereafter is etched, whereafter the micromask is ready.

The information indicating the position of the micromask during its generation relative to a laser beam incident thereon and varying in intensity and/or position, and the variation in intensity and/or position of the laser beam are fed into the control device 14.

The micromask 4 is placed in the device 1 for effecting said relative movement and is aligned in starting position therein.

The laser beam 16 is permitted to pass unmodulated through the modulator 13 and/or lens system 28,2. The laser light reflected by the substrate is permitted to pass through an expedient semi-transparent mirror 29 and is received by a light-sensitive means 30 of known kind. After having been amplified in an amplifier 31, the signal is emitted at the output of the light-sensitive means 30 to a comparison circuit 32.

Due to the reflection of the unmodulated laser beam 43 from the reflected micromask, the laser beam is modulated in a way corresponding to the way in which it was modulated at the generation of the micromask, or in other words, the way it should be modulated for generating such a micromask. The reflected laser beam 44, which is scanned by the light-sensitive means 30, thus, includes information on the pattern of the micromask in the form of a modulation.

The comparison circuit 37 comprises preferably an exclusive orgate 33.

Instead of being reflected from the micromask, the laser beam also can be caused to be transmitted and thereafter be scanned by a corresponding light-sensitive means.

Prior to starting the device 1, the position of the slides 5,8 is adjusted by the position transducers 23,19,20. The two decoders 22,24 are intended, for example, to indicate a binary "0", which indicates starting position for the slides. The output signal of each decoder 22,24 is applied to an and-gate 34, which, when the output signals are equal, emits a starting pulse via the conductor 35 to the control device 14.

The control device 14 is capable of starting the drive means 11 and stepping motor 6, whereby the position of the micromask relative to the laser beam incident thereon is changed according to a line pattern in a way corresponding to that at the generation of the micromask.

The position transducers 23,19,20 continuously emit signals vis the decoders 22,24 with respect to the position of the slides 5,8, which position corresponds to the position of said laser beam incident on the micromask relative to the micromask, to a logic circuit 36 via the conductors 39,40 and to the control device 14 via the conductors 41,42. The control device 14 is capable, on the basis of these signals, to emit a control signal in the form, for example, of acousto-optic modulator signal corresponding to the information mentioned in the introduction synchronously with the position held by the micromask relative to the incident laser light 43. Hereby, thus, the control signal is emitted synchronously with the scanned reflected light 44 or transmitted light. This control signal, which at the generation of the micromask has controlled the modulator 13, is applied to said comparison circuit 32.

The two signals thus applied to the comparison circuit 32, viz. the control signal and the signal corresponding to the reflected laser light, are compared in the circuit 32. When agreement exists between the signals thus compared, correct generation of the micromask is indicated, and in the case of disagreement between the signals inaccuracies in the generation is indicated. When the signals do not agree with one another, the comparison circuit 32 emits a signal via a conductor 37 to said logic circuit 36, which is capable then to write the position indicated by the decoders 22,24 on a recorder 38 or the like, or to feed the position into a memory. In certain cases there exists the possibility to remedy the inaccuracy on the basis of the position indication.

The logic circuit 36 may be designed, by guidance of the signal from a modified comparison circuit 33 to emit continuous signals to detect the type of the inaccuracies and to store the information in a memory 38 together with the position.

The method and device according to the invention have been described above with reference to the preferred device shown in FIG. 1 where an acousto-optic modulator 13 is provided and the slide 8 carries the optics 2. The variation in intensity and/or position of the laser beam relative to a substrate, of course, can be effected in a different way where the control signals then emitted are utilized in a corresponding manner.

The invention, thus, must not be regarded as restricted to the embodiments described above, but can be varied within its scope defined in the attached claims.

The reflected laser beam 44 or a transmitted laser beam, thus, includes information on the pattern of the micromask in the form of a modulation or signal variation at the output of the light-sensitive means 30. It is apparent that by the present invention every micromask can be quality controlled, irrespective of the device, by which it has been generated, provided that there is in a memory information with respect to the pattern of the micromask, which information, when desired, can be converted into a signal comparable with the signal occurring at the output of the light-sensitive means 30.

It was mentioned above that the control signal applied to the comparison circuit corresponds to the control signal, which was utilized during the generation of the micromask.

In this connection at least two cases can be distinguished. In the first case the micromask is generated by a laser beam, to which has been imparted via an acousto-optic modulator only intensity variations with respect to the laser beam met by the substrate. The control signal, thus, consists here of an intensity control. In this case, in the method according to the invention an unmodulated laser beam is emitted against the micromask at the same time as the control signal is applied to the comparison circuit.

In a second case the micromask is generated by a laser beam, to which has been imparted via one or two acousto-optic modulators 13 intensity variations and position variations, i.e. a scan between adjacent parallel displacements of the optics 2 relative to the substrate brought about mechanically by the slides.

In this case, at the present method, a laser beam is emitted to the micromask, which beam is controlled by the control signal to perform the same position variations as during the generation of the micromask. This part of the control signal, thus, is applied to the modulator or modulators 13, which during the generation yielded the position variations. In FIG. 1 this is effected via the conductor 15. At the same time as this part of the control signal is applied to the modulator 13, the part of the control signal which during the generation has controlled the intensity variations, is applied to the comparison circuit 32.

In both cases, thus, intensity variations are compared in the comparison circuit 32.

It is, however, possible within the scope of the invention to design the light-sensitive means 30 so as to also scan position variations. When, therefore, the control signal comprises a part for controlling position variations, even this part is applied to the comparison circuit 32, which in such a case is capable to compare both intensity and position variations.

The invention, thus, must not be regarded restricted to the embodiments described above, but can be varied within its scope defined in the attached claims.

I claim:

1. A method of inspecting the patterns of a micromask, the micromask patterns having been generated by a writing laser beam that has been both moved in certain perpendicular directions relative to the micromask and varied in intensity in response to a control signal produced from information stored in a memory, the information indicating the intensity and position of the writing laser beam relative to the micromask, the method comprising:
   A. moving said micromask relative to a laser inspection beam in the same directions as during generation of the patterns;
   B. modulating said laser inspection beam with the patterns of said micromask to form a modulated laser beam by directing said laser inspection beam onto said micromask and performing one of reflecting the modulated beam from the patterns and transmitting the modulated beam through the patterns;
   C. producing an electrical modulation signal indicating the modulation of the modulated laser beam;
   D. comparing said modulation signal with said control signal, said modulation and control signals being synchronized relative to the position of the laser inspection beam on the patterns; and
   E. providing an inspection signal indicative of correct pattern generation when said modulation and control signals agree and indicative of inaccuracies in the pattern generation when said modulation and control signals differ.

2. The method of claim 1 further including storing the position of an inaccuracy in a memory.

3. The method of claim 1 or 2 in which the variation in intensity of the writing laser beam resulted from a laser beam passing through an acousto-optic modulator controlled by an acousto-optic modulator signal and said step of comparing including comparing said modulation signal with said acousto-optic modulator signal.

4. A device for inspecting the patterns of a micromask, the micromask patterns having been generated by a writing laser beam that has been both moved in certain, perpendicular directions relative to the micromask and varied in intensity in response to a control signal produced by control means, the control means receiving information stored in memory indicating the intensity and position of the writing laser beam relative to the micromask, the apparatus comprising:
   A. laser means providing an inspecting laser beam through optics;
   B. movement means for moving at least said optics and said inspecting laser beam relative to said micromask in the same directions as during pattern generation;
   C. position means for indicating the position of the inspecting laser beam relative to the micromask;
   D. light-sensitive means producing an electrical modulation signal indicating the modulation of said inspecting laser beam by the patterns of the micromask, the modulation occurring by said inspecting laser beam being one of reflected from and transmitted through said micromask patterns;
   E. said control means emitting said control signal synchronously with the position of the inspecting laser beam indicated by the position means so that at any particular position the control signals emitted during pattern generation and inspection are the same; and
   F. comparison means for comparing said modulation signal with said control signal and emitting an inaccuracy signal indicating a deviation between the modulation and control signals.

5. The device of claim 4 further including memory means for registering the position of the inspecting laser beam relative to the micromask at which an inaccuracy signal occurs.

6. The device of claims 4 or 5 in which the laser means include an acousto-optic modulator controlled by an acousto-optic modulator signal and said comparison means compare said modulation signal with said acousto-optic modulator signal.

* * * * *